United States Patent [19]

Subramaniam et al.

[11] Patent Number: 5,690,809
[45] Date of Patent: Nov. 25, 1997

[54] IN SITU MITIGATION OF COKE BUILDUP IN POROUS CATALYSTS BY PRETREATMENT OF HYDROCARBON FEED TO REDUCE PEROXIDES AND OXYGEN IMPURITIES

[75] Inventors: Bala Subramaniam; Said Saim; Michael C. Clark, all of Lawrence, Kans.

[73] Assignee: Center for Research, Inc., Lawrence, Kans.

[21] Appl. No.: 634,293

[22] Filed: Apr. 18, 1996

Related U.S. Application Data

[63] Continuation-in-part of Ser. No. 424,872, Apr. 18, 1995.
[51] Int. Cl.$^6$ .................................................. C10G 9/16
[52] U.S. Cl. ........................... 208/48 R; 208/83; 208/91; 585/820; 585/823; 585/824; 585/450
[58] Field of Search ..................... 208/48 R, 83, 208/91; 585/820, 823, 824, 950

[56] References Cited

U.S. PATENT DOCUMENTS

| | | |
|---|---|---|
| 4,176,045 | 11/1979 | Leftin et al. . |
| 4,243,831 | 1/1981 | Malloy et al. . |
| 5,030,788 | 7/1991 | Amelse et al. . |
| 5,221,462 | 6/1993 | Reid et al. . |

OTHER PUBLICATIONS

Titscher, Melmut et al.; "A Mild and Effective Method for the Reactivation or Maintenance of the activity of Heterogeneous Catalysts", *Angew. Chem. Int. Ed. Engl.*, 20, (1981), No. 10, pp. 892–894.

Tiltscher, H. et al.; "Trends in High Pressure Chemical Reaction Engineering"; *Chem. Eng. Sci.*, vol. 42, No. 5, pp. 959–977, 1987.

Saim, Said et al.; "Isomerization of 1–Hexene on Pt/$\gamma$-Al$_2$O$_3$ Catalyst at Subcritical and Supercritical Reaction Conditions: Pressure and Temperature Effects on Catalyst Activity"; *The Journal of Supercritical Fluids*, vol. 3, No. 4, pp. 214–221, 1990.

Saim, Said et al.; "Phase and Reaction Equilibria Considerations in the Evaluation and Operation of Supercritical Fluid Reaction Processes"; *Supercritical Fluid Science and Technology*; Johnston, K.P. et al.,Eds., ACS Symposium Series No. 406, pp. 301–316 (1989).

Manos, Georgios et al.; "Coke Removal from a Zeolite Catalyst by Supercritical Fluids", *Chem. Eng. Technol.*, 14 (1991) 73–78.

Saim, Said et al.; "Isomerization of 1–Hexene over Pt/$\gamma$-Al$_2$O$_3$ Catalyst: Reaction Mixture Density and Temperature Effects on Catalyst Effectiveness Factor, Coke Laydown, and Catalyst Micromeritics", *Journal of Catalysis*, 131, 445–456 (1991).

Baptist–Nguyen, Sarah et al.; "Coking and Activity of Porous Catalysts in Supercritical Reaction Media"; *AIchE Journal*, vol. 38, No. 7, pp. 1027–1037, Jul. 1992.

Tiltscher, et al.; "Utilization of SupercriticalFluid Solvent–Effects in Heterogeneous Catalysis"; *Ber. Bunsenges. Phys. Chem.*, 88, (1984), pp. 897–900.

*Primary Examiner*—Helane Myers
*Attorney, Agent, or Firm*—Hovey, Williams, Timmons & Collins

[57] ABSTRACT

An improved process is provided for in situ mitigation of coke buildup and porous catalyst used for the processing of hydrocarbon feed stocks. The process exhibits improved catalyst activity over extended periods and the process comprises the pretreatment of hydrocarbon feed stocks to reduce impurities in the feed stocks in the form of peroxides and oxygen compounds that promote the formation of coke precursors, which precursors are typically in the form of olefinic oligomers. The process includes contacting the pretreated feed stream with a suitable catalyst under subcritical, near-critical and supercritical conditions.

13 Claims, 6 Drawing Sheets

IN SITU MITIGATION OF COKE BUILDUP IN POROUS CATALYSTS BY PRETREATMENT OF HYDROCARBON FEED TO REDUCE PEROXIDES AND OXYGEN IMPURITIES

RELATED APPLICATIONS

This is a continuation-in-part of application Ser. No. 08/424,872, filed Apr. 18, 1995, entitled In Situ Mitigation of Coke Buildup in Porous Catalysts with Supercritical Reaction Media. The teachings of application Ser. No. 08/424,872, are incorporated herein by reference.

1. Field of the Invention

The present invention broadly relates to the mitigation of coke formation on catalysts in contact with hydrocarbons at elevated temperatures and pressures. In particular, this invention relates to the in situ mitigation of coke buildup in porous catalysts by pretreatment of hydrocarbon feed to reduce peroxides and oxygen impurities.

2. Background of the Invention

Many industrially significant catalytic reactions such as isomerization, disproportionation of aromatics and alkylation reactions on acid catalysts are characterized by catalyst deactivation due to coke build-up on the catalyst.

Coking of acid catalysts is typically caused by side reactions that involve mainly acid-catalyzed polymerization and cyclization of olefins that produce higher molecular-weight polynuclear compounds which undergo extensive dehydrogenation, aromatization and further polymerization. These products are generally termed as coke and have been characterized as either "consolidated" carbon deposits (that cannot be dissolved in organic solvents) or "mobile" deposits which are precursors of the consolidated deposits. For example, in the case of reforming catalysts, the mobile deposits are typically polyaromatic hydrocarbons.

The primary reasons for coke buildup leading to catalyst deactivation, are the relatively low volatilities of the mobile coke compounds that are initially formed in the low sub-critical densities (and hence low coke solubilizing power) of the gas-phase reaction mixture. The relatively low volatilities of the mobile coke compounds at gas phase reaction conditions results in the strong adsorption of these compounds on the catalysts leading to their progressive transformation to consolidated coke. The consolidated coke buildup eventually plugs the pores of the support matrix, in which the catalyst particles reside, and causes total deactivation of the catalyst. The coked catalyst must then be regenerated, typically by air oxidation of the coke exposing the catalyst to high temperatures (400°–500° C.), which can often cause thermal degradation of the catalyst.

Much has been reported in the literature on the subject of supercritical operational effects upon coke formation and extraction, and corresponding trends in catalyst deactivation and reaction kinetics. These teachings, however, are in many respects inapplicable to industrially significant catalytic reactions because they often overlook critical coke formation and extraction mechanisms, and mass transport effects on catalyst effectiveness and catalyst deactivation rates under supercritical conditions. For example, for 1-hexene reaction on a low activity, macroporous shell γ-$Al_2O_3$ catalyst (having an active specific surface of 4.95 $m^2/g$), Tiltscher et al. *Angew Chem. Int. Ed* 20:892(1981) teaches that reactor operation at supercritical conditions leads to steady state catalyst activity maintenance. The teaching is inapplicable to industrially significant reactions because the study employed shell catalysts having a catalytically active specific surface of 4.95 $m^2/g$. The shell catalyst configuration was used apparently to avoid pore diffusion limitations for the purpose of studying coke extraction mechanism associated with supercritical fluids. Industrially significant reactions often require highly porous catalysts having effective surface areas greater than 150 $m^2/g$.

Tiltscher et al. *Chem. Engng. Sci.* 42:959 (1987) teaches that the regeneration of highly porous catalysts (500 $m^2/g$) by supercritical fluids involves a much more complex mechanism (when compared to that associated with the shell catalyst referenced above having low catalytically active specific surface) because of pronounced internal transport processes. This reference, however, teaches that catalyst activity in the sub-critical range is higher than activity in the supercritical range (though the deactivation rate in the sub-critical is also higher).

Saim and Subramaniam *J. Supercrit. Fluids* 3:214 (1990) and Saim and Subramaniam *J. Catal.* 131:445 (1991) investigated 1-hexene isomerization on a high activity, high surface area, commercial Pt/γ-$Al_2O_3$ catalyst in a 300 ml CSTR at near-critical temperatures (1.01 $T_c$ and 1.1 $T_c$). At both temperatures, the authors reported that end-of-run isomerization rates decrease with isothermal increases in pressure in the sub-critical region and moderate supercritical regions, and increase with pressure in the dense supercritical region ($p_r$>1.7). However, the catalyst deactivated with time even at supercritical conditions. These teachings are not applicable to industrially significant reactions because, as the authors noted, a significant portion of the catalyst activity was lost due to buildup of consolidated, unextractable coke during the sub-critical phase of reactor fill-up. These references are also inapplicable to industrially significant reactions because it teaches that steady state catalyst activity conditions may be achieved, but at the expense of a lower reaction rate for the desired reaction.

Manos and Hoffman *Chem. Eng. Technol.* 14:73 (1991), based on coke desorption rates and thermodynamic analysis of the solubilities of model coke compounds (such as polyaromatic hydrocarbons) in SCFs, concluded that while complete in situ reactivation of a zeolite catalyst by SCFs is impossible, the catalyst deactivation rate can be reduced. The authors observed that only freshly formed coke precursors could be dissolved by the SCF reaction medium and confirmed that rapid start-up was essential to avoid the formation of consolidated, unextractable coke during the sub-critical phase of pressure buildup. This reference does not teach that the deactivation rate can actually increase in supercritical regions for highly porous catalysts. Thus, this reference teaches that complete coke removal by supercritical fluids is impossible but that catalyst deactivation could be slowed down under supercritical conditions.

By developing a single-pore model for coke formation and in situ coke extraction, Baptist-Nguyen and Subramaniam, AICHE J., 38:1027 (1992), show that for an isothermal increase in pressure along a near-critical isotherm (1.01 $T_c$, there exists an optimum pressure (i.e., reaction mixture density) at which catalyst activity is maximized. At lower densities, the catalyst undergoes deactivation due to a lack of coke extraction while at higher than optimum densities the catalyst activity decreases due to pore diffusion limitations in liquid-like reaction mixtures. This reference teaches that all coke is removed when operating beyond optimum conditions noted in this reference and that catalyst activity reaches a steady state value beyond optimum conditions.

Various processes are known to inhibit coke formation in other certain processing environments. For example, U.S.

Pat. No. 4,176,045 discloses a process for the production of olefins by steam cracking, during which process coke deposits in cracking furnace tubes is minimized by the addition of low-coking hydrocarbon to fresh feed having a high-coking tendency.

U.S. Pat. No. 5,221,462 discloses a method for inhibiting the formation and deposition of coke on heated metal surfaces in contact with a hydrocarbon feed stock undergoing pyrolytic processing to produce lower hydrocarbon fractions where metal surfaces have a temperature of about 1600°F., which method comprises adding to the hydrocarbon feed stock being processed a coke inhibiting amount of dyhydroxybenzene compound.

Problems also arise during conventional reactor operations during start-up and shut-down procedures. Such procedures often lead to rapid coking (by the same mechanisms discussed above) and catalyst deactivation because these procedures expose the catalyst to sub-critical reaction mixtures, therefore requiring either frequent catalyst regeneration or a continuous supply of fresh catalyst to the reactor.

Accordingly, the requirements are exceedingly stringent for successfully mitigating coke buildup on catalyst surfaces exposed to hydrocarbons at elevated temperatures and pressures.

SUMMARY OF THE INVENTION

The present invention overcomes the problems outlined above, and provides an improved process employing in situ mitigation of coke buildup in porous catalysts with sub-critical, near-critical and supercritical hydrocarbon and oxygen impurities (between $C_1$–$C_{20}$) reaction media. More particularly, the invention employs a process for pretreatment of the hydrocarbon feed to reduce peroxide impurities and which deoxygenates the feed to reduce peroxide formation at reaction conditions.

The invention is predicated upon the discovery that the reduction in olefinic oligomer formation in the fluid phase, in conjunction with enhanced in situ extraction of coke-forming compounds (as stated above), further reduces coke laydown and thereby further improves catalyst pore accessibilities and rates of desired reactions. There are three pathways for the formation of olefinic oligomers, which are prolific coke producers. The pathways include formation of such oligomers: (i) in the bulk fluid phase via catalysis of the hydrocarbon feed by peroxides (organic and inorganic) and other oxygen impurities present in the feed; (ii) in the reactor via catalysis of the hydrocarbon feed on the acid sites of the catalyst; and (iii) in the reactor via catalysis of the hydrocarbon feed on the metal surfaces of the reactor.

Oligomers formed in the fluid phase are prolific coke precursors and become an important consideration in supercritical reaction operations because oligomer formation steadily increases with pressure. Oligomer formation can amount to as much as 2wt % of effluent product streams at supercritical pressures corresponding to a reduced density of the reaction media in excess of about 1.7.

In accordance with the present invention, therefore, a method is provided to minimize catalyst deactivation rate and coke laydown by providing a hydrocarbon feed stream and pretreating the feed stream to reduce the level of peroxide impurities in the stream. The feed stream may also undergo deoxygenation by means of bubbling helium, or other suitable medium, through the feed stock which supplies the feed stream. Preferably, the feed stream undergoes both pretreatment to reduce peroxide impurities and deoxygenation. (In some processes, feed streams intentionally include oxygen containing species for the formation of desired reaction products. Consequently, the deoxygenation step of the invention would not be employed with such streams containing oxygen species. Stated another way, deoxygenation is directed only to feed streams where oxygen species are considered as impurities.) Thereafter, the feed stream is brought into contact with a catalyst under suitable conditions to generate desired reaction products.

In more detail, peroxide impurities are removed from hydrocarbon feed by pretreatment of the feed with an adsorption media or other suitable agents that prevent peroxides (organic and inorganic) from participating in olefinic oligomer formation reactions. The adsorption media is preferably activated alumina. Peroxides are reduced to less than 100 ppm, and preferably less than 50 ppm, in the feed stock stream.

In another aspect of the invention, oligomer formation may be mitigated by employing reactors with passivated surfaces, preferably by coating internal reactor surfaces with silico steel.

In yet another aspect of the invention, the pretreated and deoxygenated feed may be brought into contact with catalyst under sub-critical conditions, but is preferably brought into contact with catalyst under near-critical and supercritical conditions.

DETAILED DESCRIPTION OF THE DRAWINGS

DETAILED DESCRIPTION

The following examples set forth preferred compositions in techniques for practicing the instant invention, as well as test results demonstrating effectiveness. It is also to be understood, however, that these examples are presented by way of illustration only and nothing therein shall be taken as a limitation upon the overall scope of the invention.

Experimental Apparatus and Procedures

The isomerization of 1-hexene over a 1/16" Pt/γ-$Al_2O_3$ (Engelhard E-302) reforming catalyst was investigated in the examples. The Pt loading on the catalyst is 0.6 wt. %. The catalyst was pretreated off-line in flowing helium at 100 sccm at 330° C. for 18 h, followed by hydrogen also at 100 sccm at 330° C. for 4 h. The pretreated catalyst has a BET surface area of 188 m²/g, total pore volume of 0.42 cc/g and an average pore radius of roughly 50 Å. Approximately 1 g of the dried pretreated catalyst was loaded into the reactor before each run. The catalyst was treated further on-line at 330° C. by flowing helium at 100 seem for 2 h, followed by hydrogen at 100 sccm for 2 h at 330 ° C. The reaction experiments in the examples presented below were carded out at 281° C. (1.1 $T_c$) with pressures ranging from atmospheric (0.032 $P_c$) to 70 bars (2.2 $P_c$). The densities of the reaction mixture vary from gas-like to liquid-like in this pressure range.

Figure 1:
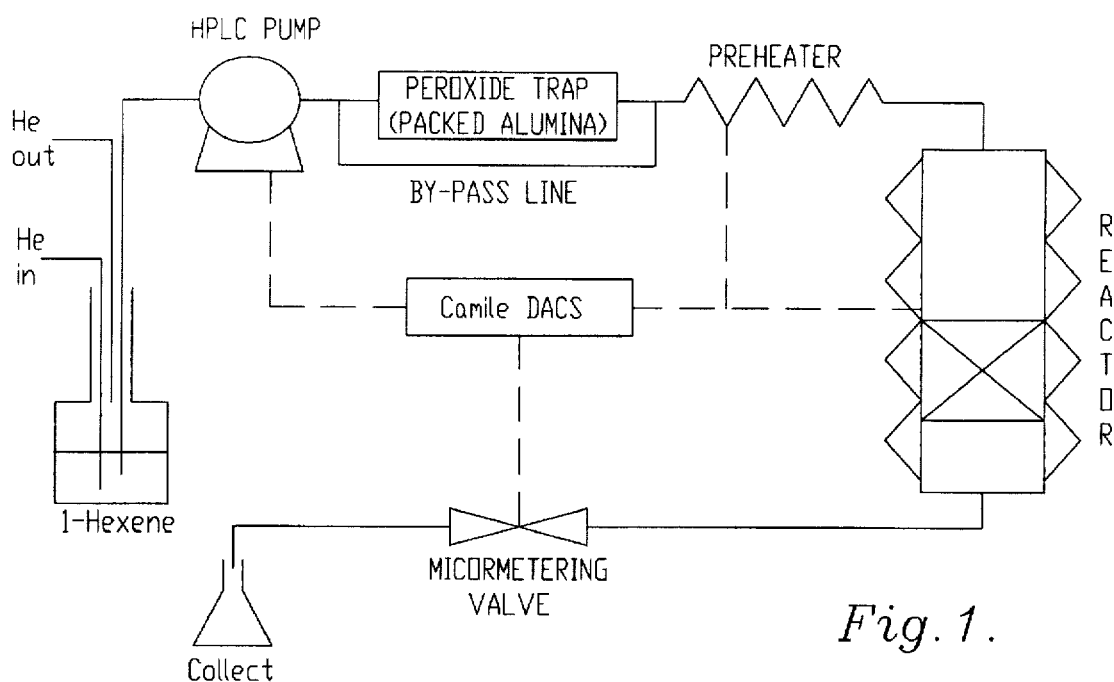
FIG. 1 is a schematic of the experimental apparatus employed in the examples.

FIG. 1 shows a schematic of the experimental reactor unit 10. The 1-hexene feed (Ethyl Corporation; Lot #PT060592) is contained in an opaque bottle 12 to minimize possible peroxide formation due to exposure to light. The feed is continuously maintained deoxygenated by bubbling helium fed via line 14 to bottle 12 and through the hexene feed such that the head space 16 is always blanketed with helium.

The 1-hexene feed is pumped from bottle 12 through line 18 to the suction of HPLC pump 20, and thereafter through line 22 to peroxide trap 24. Peroxide trap 24 is a stainless steel tube packed with 52 g of dry activated neutral alumina (Scientific Adsorbents Incorporated, Lot #A25M1).

The alumina-treated feed passes the rough 1/16" stainless steel lines to a safety head (burst pressure of 400 bar at 20° C.).

The feed exits the alumina trap 24 via line 26 and flows through preheater 28 and line 30 into reactor 32. Bypass line 34 joins line 22 and 26 and permits feed to bypass the peroxide trap 24. Reactor 32 is a stainless steel tubular reactor (15 ml capacity). Once entering reactor 32, the feed passes over a 3.5 cm long catalyst bed supported by stainless steel screens. Thermocouples monitor 36 the temperature of the feed entering the reactor, and the temperatures at the top and bottom of the catalyst bed. These measurements provide feedback for PID control of the preheater and reactor temperature via a Camile® Data Acquisition and Control System 38. The reactor 32 temperature overshoot during reactor startup is less than 10° C. and the bed temperature is controlled within ±1° C. during the examples.

The reactor effluent exits reactor 32 via line 40 and flows through a stepper-motor-driven, computer-actuated micrometering valve 42 (Autoclave Engineers #30VRMM) which is used to control reactor pressure. The automated control of the valve 42 is described in more detail elsewhere (Subramaniam and Jooma, 1995). The reactor effluent exits valve 42 and flows through line 44 into collection bottle 46.

For all the runs described in the examples, reactor pressure fluctuations were within transducer precision (±0.5 bar).

The 1-hexene feed employed in the examples contained roughly 130 ppm of peroxides, expressed as ppm oxygen. Pretreatment by passing through an alumina packing reduces the peroxide content to 2 ppm or less. For achieving this level of peroxide reduction, one gram of alumina is needed for roughly 30 grams of the hexene feed stock. For the hexene feed rate employed in our studies (135 g/h), the alumina packing can effectively adsorb peroxide impurities for 13 h. For extended runs, the feed was pretreated off-line.

The reactor effluent is sampled at various times throughout the run and is analyzed for 1-hexene, its isomers and oligomers using a HP5890 GC/FID instrument. At the end of a given run (lasting from 3 to 42 h), the catalyst is removed from the reactor and subjected to gravimetric analysis (to determine coke laydown) and to micromeritics analysis (to determine reduction in surface area and pore volume due to coking) with a Gemini 2000 Pore Volume and Surface Area analyzer. Samples were analyzed for peroxide content using a wet technique obtained from Ethyl Corporation (ASTM Method D3703-92).

In each of the examples presented below, apparatus 10 was operated as previously described and under the conditions and parameters as further set forth in each of the particular examples.

EXAMPLE 1

The effect of alumina pretreatment of 1-hexene feed on hexene conversion at sub-critical and supercritical conditions.

Figure 2:
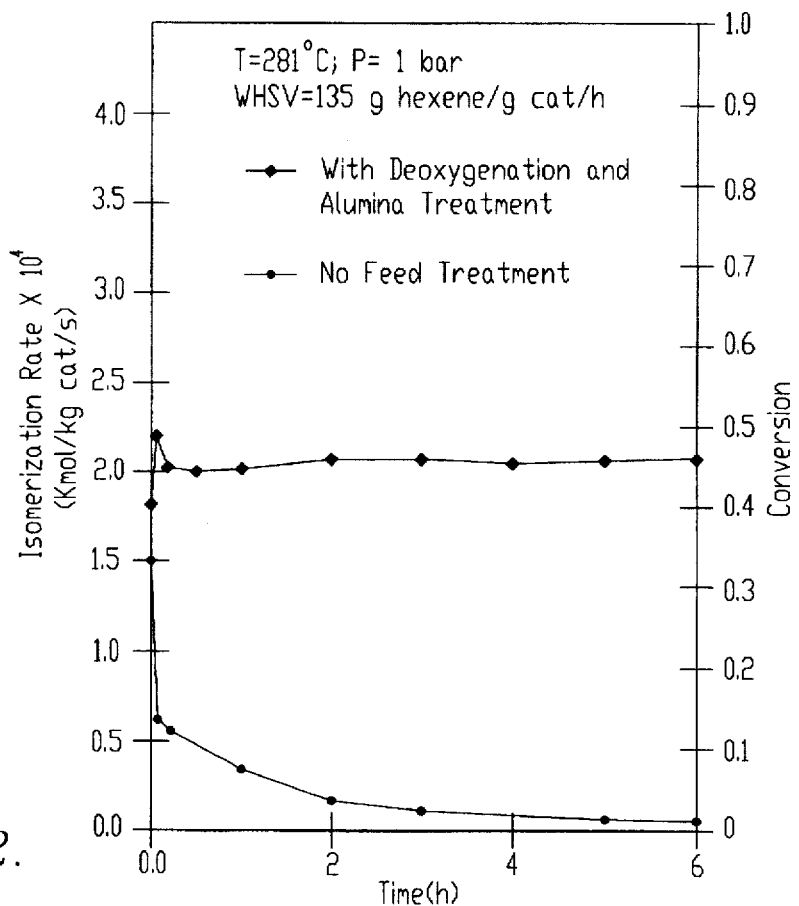
FIG. 2 is a plot showing the effect of feed treatment with alumina on catalyst activity at sub-critical conditions.
Figure 3:
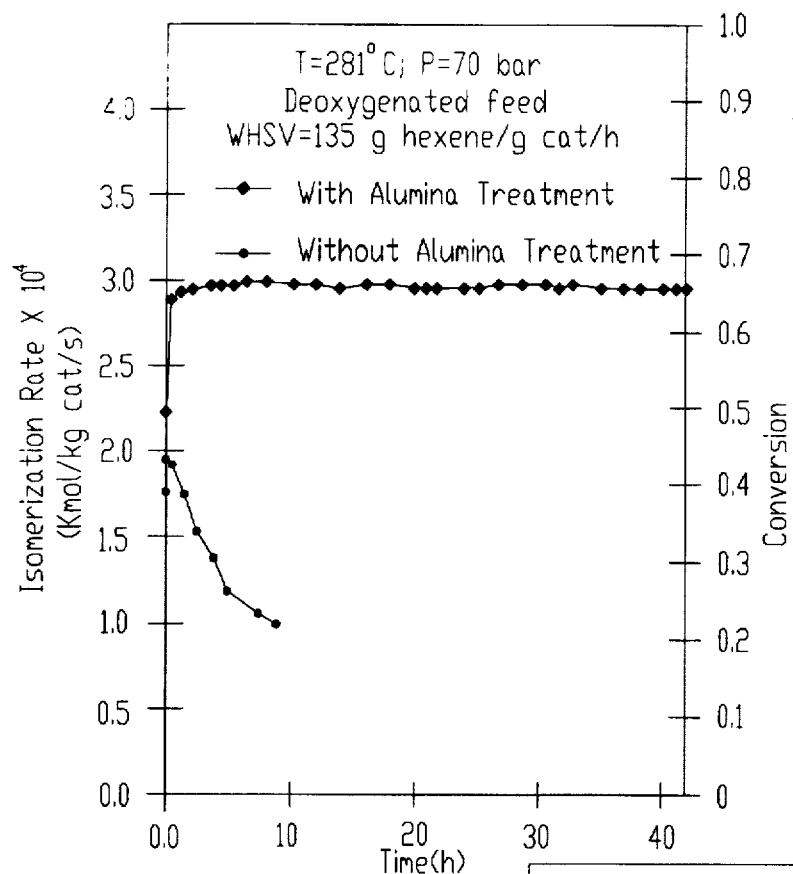
FIG. 3 is a plot showing the effect of feed treatment with alumina on catalyst activity at supercritical conditions.

In example 1, there were four runs. In the first two runs, the reactor was maintained at the following conditions: T=281° C.; P=I bar; WHSV=135 g hexene/g cat/h (FIG. 2). In the first run, the feed underwent deoxygenation and alumina pretreatment. In the second run, the feed was not pretreated to remove peroxides or oxygen impurities. In the third and fourth runs, the reactor was maintained at the following conditions: T=281° C.; P=70 bar; WHSV=135 g hexene/g cat/h (FIG. 3). In both the third and fourth runs, the feed was deoxygenated. The feed in the third run, underwent alumina pretreatment and the feed in the fourth run underwent no alumina pretreatment.

FIGS. 2 and 3 shown the effect of alumina pretreatment of the 1-hexene feed on hexene conversion at sub-critical and supercritical conditions for identical space velocities. The feed was continuously deoxygenated by bubbling helium through it. Without alumina pretreatment, the catalyst undergoes almost total deactivation in about 6 hours at sub-critical conditions (FIG. 2). However, when the 1-hexene feed stock is pretreated in an alumina packing prior to entering the preheater, significantly higher conversions (~45%) are obtained. At supercritical conditions (FIG. 3), while higher initial hexene conversions (~45%) are attained, the catalyst undergoes significant deactivation in the absence of alumina treatment. With alumina pretreatment however, nearly constant conversion (~65%) is observed even during an extended run lasting 42 hours.

EXAMPLE 2

The effect of pretreating feed to remove only peroxides.

Figure 4:
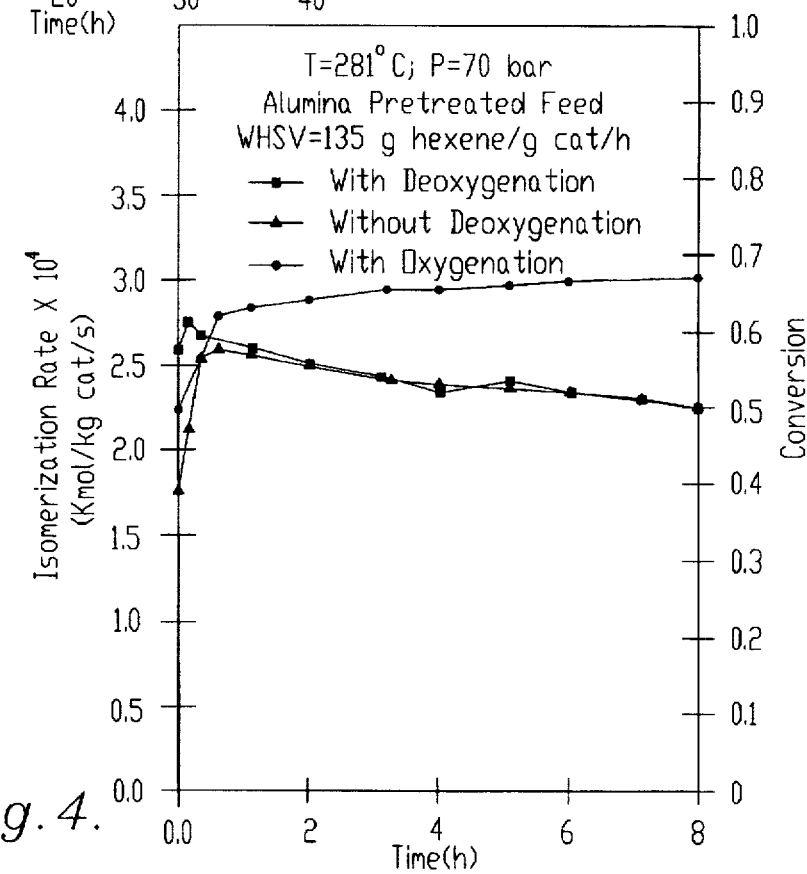
FIG. 4 is a plot showing the effect of dissolved oxygen in catalyst activity at supercritical conditions.
Figure 5:
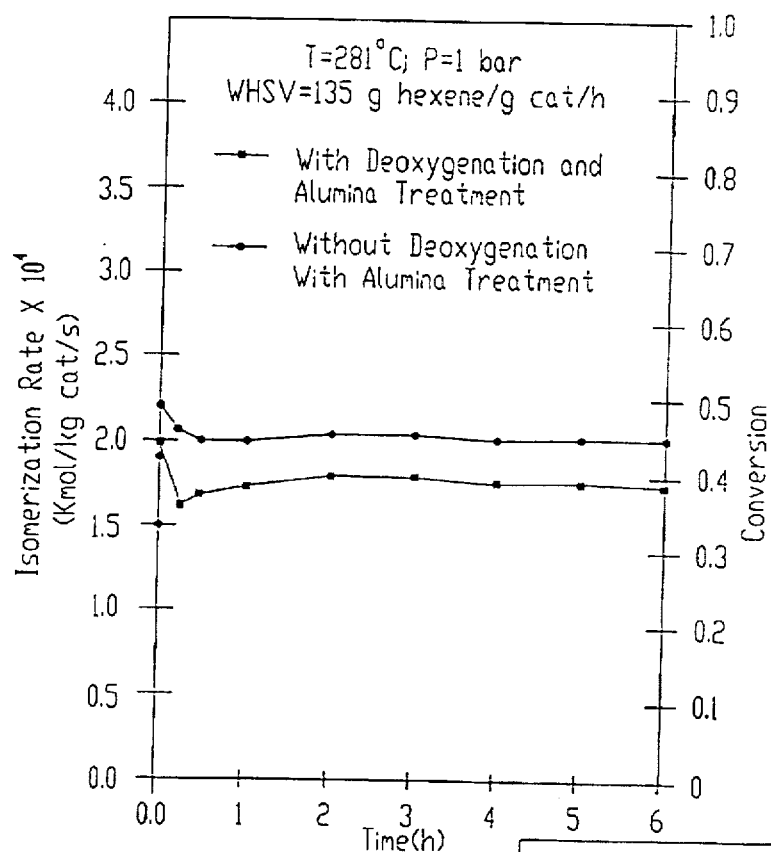
FIG. 5 is a plot showing the effect of dissolved oxygen on catalyst activity at sub-critical conditions.

In example 2, there were five runs. In the first three runs, the feed underwent alumina pretreatment and the reactor was maintained in the following conditions: T=281° C.; P=70 bar; WHSV=135 g hexene/g cat/h (FIG. 4). In two of the first three runs, the feed underwent no deoxygenation. In the fourth and fifth runs, the reactor was operated at the following conditions: T=218° C.; P=1 bar; WHSV=135 g hexene/g cat/h (FIG. 5). In the fourth run, the feed underwent both deoxygenation and alumina pretreatment. In the fifth run, the feed underwent alumina pretreatment without deoxygenation. When the feed is pretreated with alumina but not deoxygenated, the catalyst deactivates gradually as shown in FIG. 4, with conversion falling to 50% after eight hours at 70 bar. Conversions obtained with a 1-hexene feed subjected to continuous oxygenation showed a nearly identical deactivation trend over an eight hour duration. In contrast, feed oxygenation or deoxygenation has a relatively minor effect on hexene conversion with time at 1 bar as long as the feed is pretreated with alumina (FIG. 5). It is theorized that the formation of peroxides by dissolved oxygen in the feed is much faster at higher pressures than at atmospheric pressure. These peroxides, which are formed mainly in the preheater and the reactor sections of the apparatus, catalyze the formation of olefinic oligomers leading to an increased rate of coke formation, and consequently, catalyst deactivation.

As summarized in Table 1, there is neither measurable coke laydown nor surface area/pore volume losses in catalyst exposed to alumina-pretreated and deoxygenated feed. However, a small amount of coke, with correspondingly minor pore volume and surface area losses, was observed on catalyst exposed to alumina pretreated but non-deoxygenated feed. These data along with the hexene conversion histories demonstrate that alumina pretreated and feed deoxygenation promote nearly-constant activity maintenance.

roughly equal to the amount of peroxides formed in the absence of the catalyst (i.e., in the bulk fluid phase). It is clear that the increased oligomer production in the fluid phase when the alumina trap is bypassed triggers the observed catalyst deactivation.

EXAMPLE 5

Comparison of hexene oligomers in the effluent stream with and without alumina pretreatment of the feed.

In example 5, the first four runs were conducted without catalyst present. In the first and second run, pressure was maintained at 1 bar and in the third and fourth runs, the pressure was maintained at 70 bar. In the first and third runs, the peroxide level in the feed was 2 ppm, and in the second and fourth runs, the peroxide level in the feed was 130 ppm.

In the fifth through eighth runs, catalyst was present. In the fifth and sixth runs, pressure was maintained at 1 bar and

TABLE 1

Effect of feed oxygenation and operating pressure on coke laydown, surface area and pore volume.

| Catalyst property | Pretreated catalyst | With feed deoxygenation (70 bar) | Without feed deoxygenation (70 bar) | With feed deoxygenation (1 bar) | Without feed deoxygenation (1 bar) |
|---|---|---|---|---|---|
| Coke laydown (% of fresh) | — | [1]0 | 3.00 | [1]0 | 1.35 |
| BET surface area (m$^2$/g) | 188 | 187 | 181 | 188 | 175 |
| Pore volume (cc/g) | 0.42 | 0.42 | 0.38 | 0.42 | 0.38 |

[1]less than 0.3% wt. loss observed.

EXAMPLE 3

The effect of peroxides on isomerization.

Figure 6:
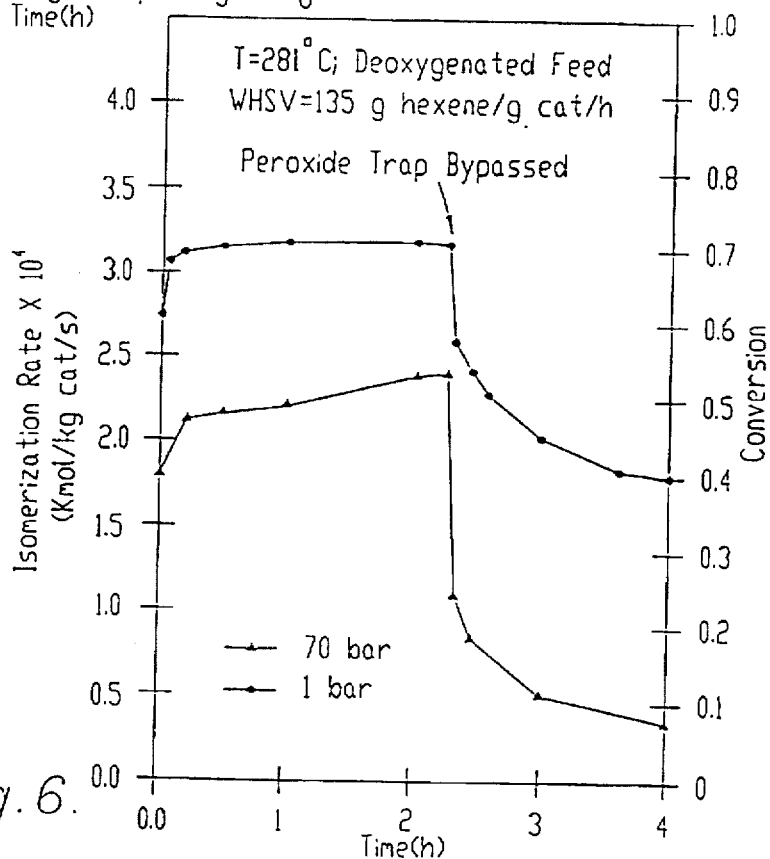
FIG. 6 is a plot showing the effects of peroxides on isomerization rate.

In example 3, there were two runs and the reactor was maintained at the following conditions: T=281° C.; WHSV=135 g hexene/g cat/h (FIG. 6). In the first run, the pressure was maintained at 70 bar and in the second bar the pressure was maintained at 1 bar.

As shown in FIG. 6, when the peroxide trap is intentionally bypassed after roughly two hours into a run, a sharp drop in 1-hexene conversion occurs. At four hours into the run, the conversion decreases to 40% at 70 bar and to about 8% at 1 bar.

EXAMPLE 4

The effect of peroxides on oligomers in reactor effluent.

Figure 7:
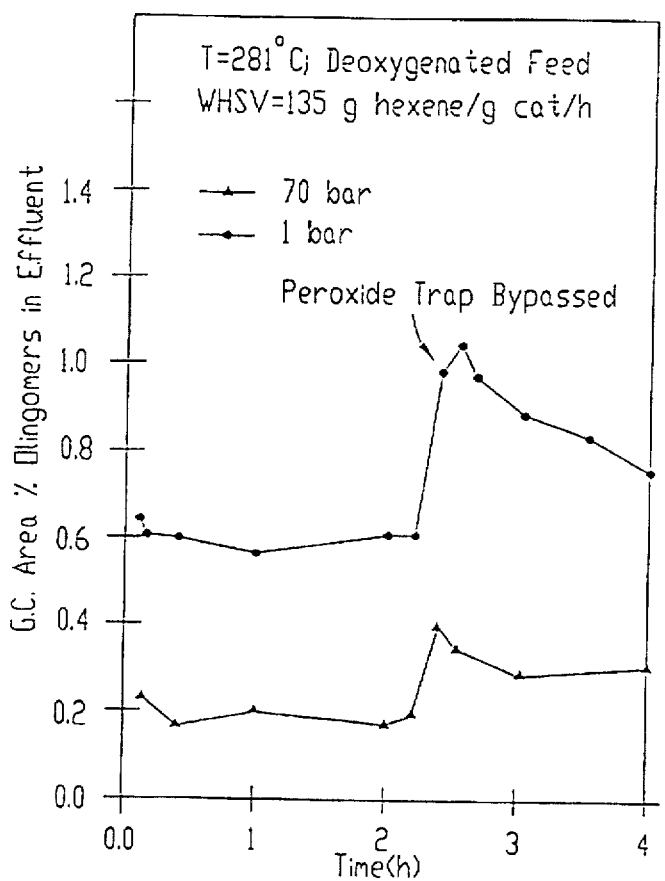
FIG. 7 is a plot showing the effect of peroxides on oligomers in the reactor effluent.

In example 4, there was a first run (P=70 bar) and a second run (P=1 bar). In both runs, the reactor was maintained at the following conditions: T=281° C.; WHSV=135 g hexene/g cat/h (FIG. 7). In both runs, the feed was deoxygenated.

As shown in FIG. 7, the drop in 1-hexene conversion is accompanied by an initial increase in total oligomers in the effluent stream. With time, the oligomer concentration passes through a maximum. Thereafter, as the catalyst deactivates, the total amount of oligomers also decreases. This decline indicates that the oligomer formation occurs via two pathways: one via peroxide radicals in the fluid phase and the other on acid sites of the catalyst. (Oligomer formation on the metal surfaces of the reactor was found to be negligible in comparison to oligomer formation via the other two pathways.) Oligomer formation on the catalyst will therefore decrease as the catalyst deactivates. The increase in oligomers after the peroxide trap is bypassed is in the seventh and eighth runs, pressure was maintained at 70 bar. In the fifth and seventh runs, the peroxide level in the feed was 2 ppm, and in the sixth and eighth runs, the peroxide level in the feed was 130 ppm.

Figure 8:
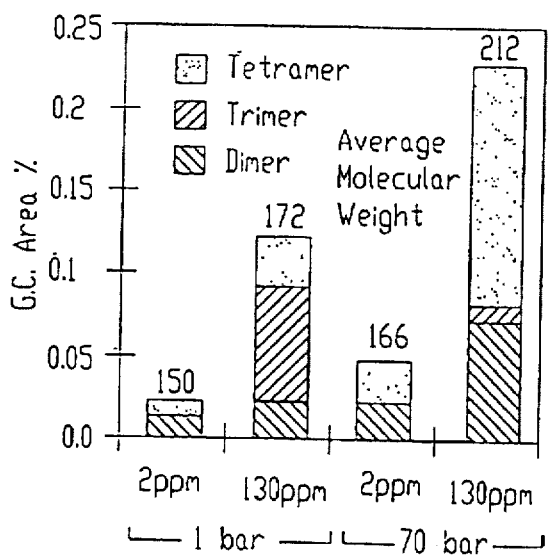
FIG. 8 is a plot showing oligomers in effluent without the catalyst present.
Figure 9:
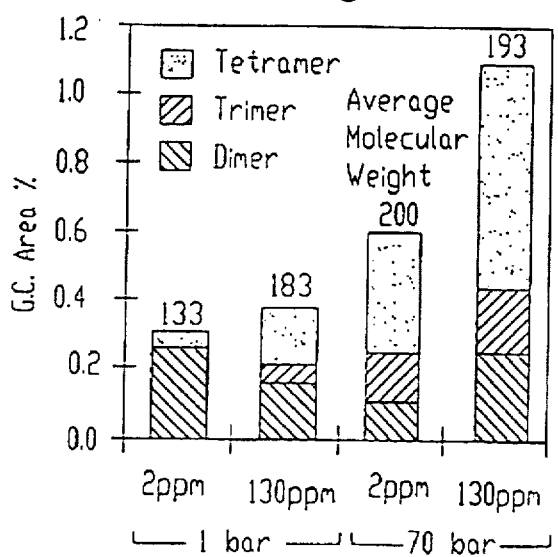
FIG. 9 is a plot showing oligomers in effluent with catalyst present.

FIG. 8 and 9 provide a comparison of the hexene oligomers in the effluent stream with and without alumina pretreatment of the feed. At 1 bar and in the absence of catalyst (FIG. 8), significant amounts of hexene oligomers are observed when 130 ppm of peroxides are present in the feed. There is a fivefold decrease in total oligomer formation when the peroxide content is reduced to 2 ppm at both sub-critical and supercritical conditions. In the presence of catalyst (FIG. 9), a substantial amount of oligomers is found in the effluent even with the reduced peroxide feed, indicating that there is significant oligomer formation on the catalyst. The oligomer content in the presence &catalyst when the peroxide trap is bypassed (the second and fourth bars from the left in FIG. 9) corresponds to the maxima in FIG. 7.

When the reactor pressure is increased from 1 to 70 bars, there is a 50% increase in total oligomers with the reduced peroxide feed in the absence of the catalyst (FIG. 8). In the presence of 130 ppm peroxides in the feed, a twofold increase in the total oligomer content is observed in the absence of catalyst. In the presence of catalyst, however, the oligomer content in the effluent increases by roughly an order of magnitude with the reduced peroxide feed (FIG. 9). This again indicates significant oligomer formation on the catalyst. However, because of enhanced desorption of the coke-forming compounds in supercritical reaction mixtures, the catalyst activity is nearly constant (see FIG. 3). When the peroxide trap is bypassed, the catalyst deactivates as discussed earlier. Presumably, the oligomer removal rate is offset by the increase in oligomer formation rate leading to coke formation, and therefore, catalyst deactivation.

As shown in FIGS. 8 and 9, up to hexene tetramers are detected in the reactor effluent. The distribution of the hexene oligomers is strongly influenced by the peroxide content and the operating pressures. In general, higher order oligomers are favored with increasing peroxide content and pressure, as reflected by the approximate weight-average molecular weights. In the presence of the catalyst, however, similar oligomer distributions are found at both peroxide levels at 70 bar, and at 130 ppm at both pressures.

From the normal boiling points of similar model compounds (Table 2), it is clear that the volatilities of the dimers are trimers are high at the reaction temperature (281° C.). In contrast, the relative volatilities of model compounds similar to the tetramers (such as tetraoctasone) are lower resulting in their enhanced adsorption at sub-critical conditions and an increased likelihood of their transformation to consolidated coke.

TABLE 2

Normal boiling points of coke precursors and similar compounds

| Compound | # Carbon Atoms | Normal Boiling Point (°C.) |
|---|---|---|
| 1-Hexene | 6 | 63 |
| Dodecane | 12 | 216 |
| Octadecane | 18 | 316 |
| Tetracosane | 24 | 391 |

EXAMPLE 6

Catalyst activity regeneration by supercritical and sub-critical reaction mixtures.

In example 6, there were two runs. In both runs, the feed was deoxygenated and the peroxide trap was bypassed for nearly 30 minutes after roughly an hour into the run. In the first run (FIG. 10), the reactor was maintained at the following supercritical conditions: T=281° C.; P=70 bar; WHSV=135 g hexene/g cat/h. In the second run (FIG. 11), the reactor was maintained at the supercritical conditions: T=281° C.; P=I bar; WHSV=135 g hexene/g cat/h.

Figure 10:
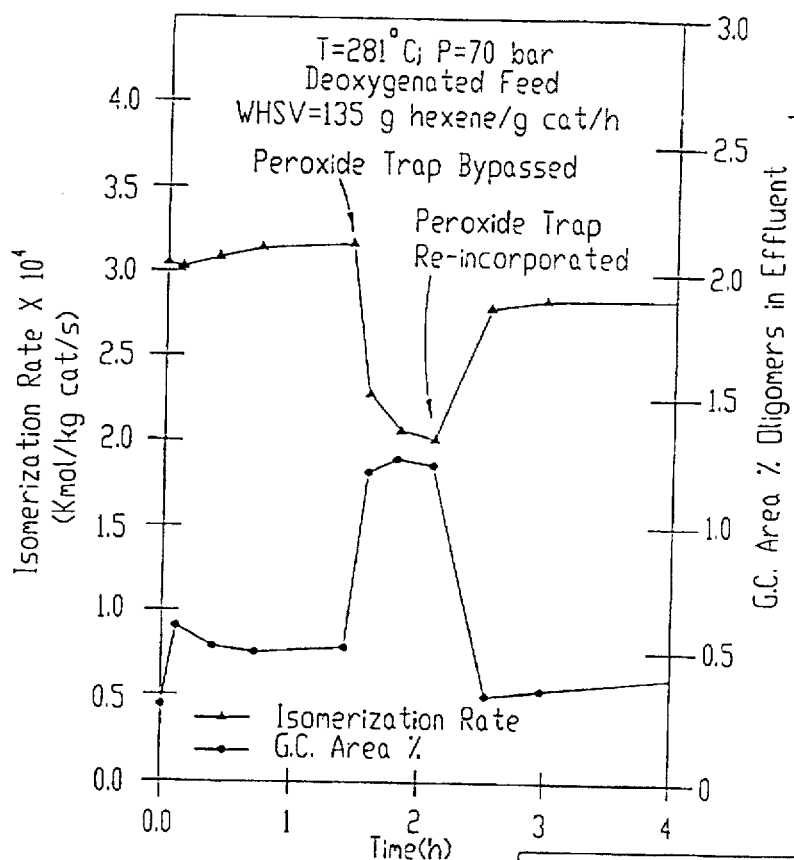
FIG. 10 is a plot showing activity recovery at supercritical conditions.
Figure 11:
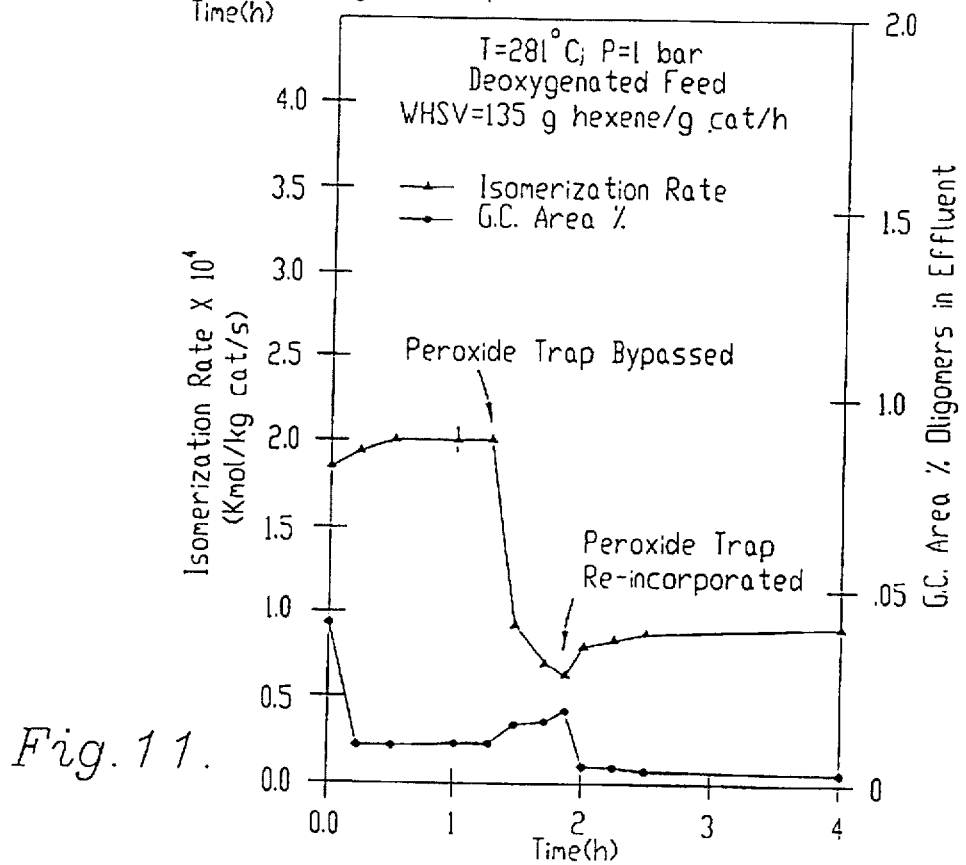
FIG. 11 is a plot showing activity recovery at sub-critical conditions.

FIGS. 10 and 11 show the extent of catalyst activity regeneration by supercritical and sub-critical reaction mixtures respectively. As before, the catalyst activity decreases dramatically in both cases accompanied by a concomitant increase in the effluent oligomer amounts. When the feed is rerouted through the peroxide trap, nearly 70% of the lost activity is restored at supercritical conditions as compared to only 20% at sub-critical conditions.

While nearly constant hexene conversions are observed at both conditions following reincorporation of the peroxide trap, the catalyst exposed to sub-critical reaction mixtures had undergone more extensive deactivation when the peroxide trap was bypassed. From an operational standpoint, supercritical reaction mixtures are therefore more desirable to restore catalyst activity loss caused by temporary increases in the peroxide content of the feed.

EXAMPLE 7

Pressure and particle size effect on isomerization rate.

In example 7, there were three runs. In the first run, the feed underwent alumina pretreatment and deoxygenation. The reactor was maintained at the following conditions: T=281° C.; WHSV=135 g hexene/g cat/h; extrudates size= $\frac{1}{16}$". In the second and third runs, the feed underwent alumina pretreatment and deoxygenation. The reactor was maintained at the following conditions: T=281° C.; WHSV= 135 g hexene/g cat/h. In the second run, the catalyst was 40–60 Mesh. In the third run, the catalyst was $\frac{1}{16}$" extrudates.

Figure 12:
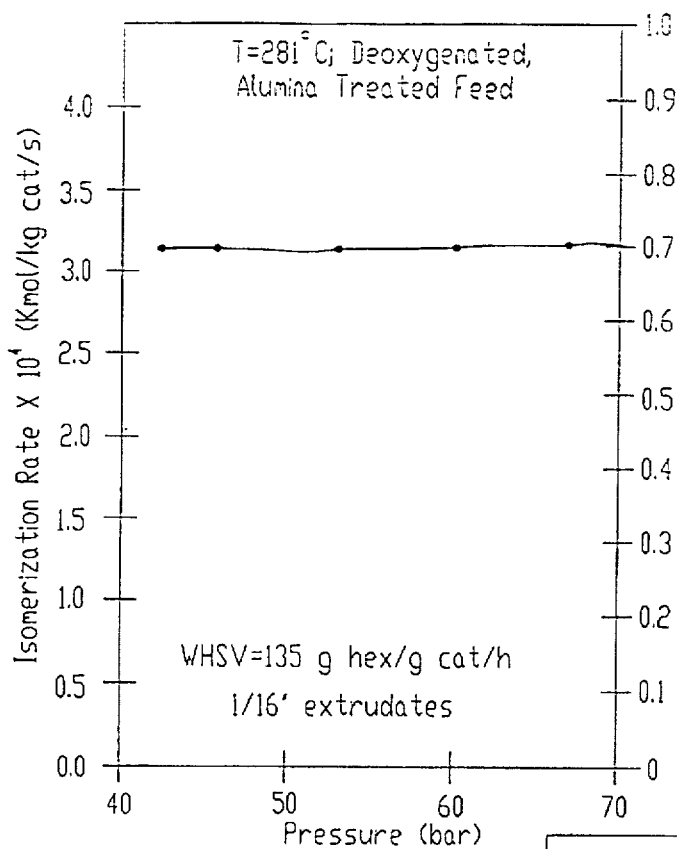
FIG. 12 is a plot showing pressure effect on isomerization rate.
Figure 13:
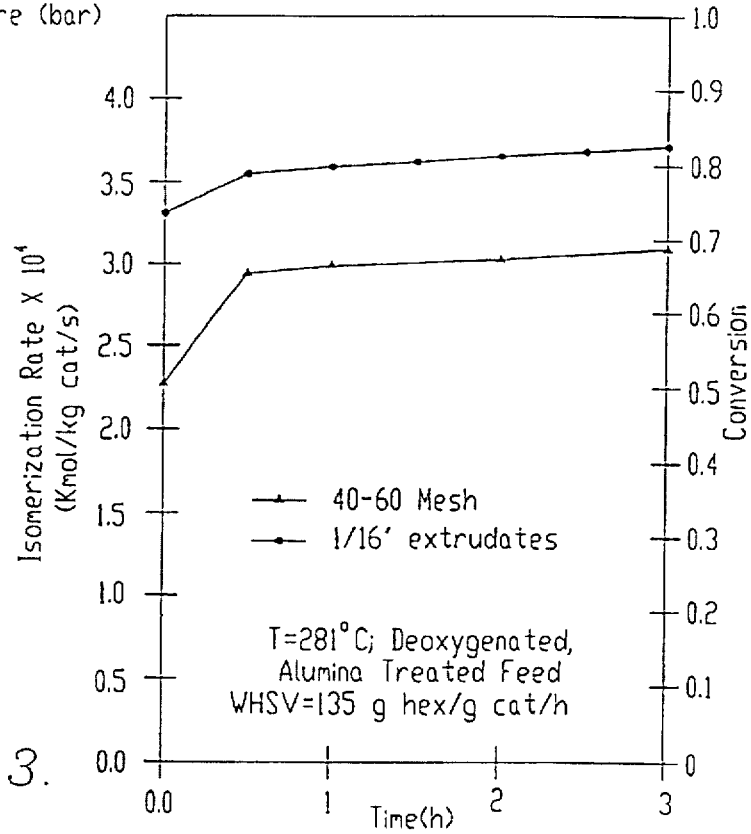
FIG. 13 is a plot showing particle effect on isomerization rate.

The nearly constant conversions at several supercritical pressures (FIG. 12), as well as the increase in conversion with a decrease in catalyst size (FIG. 13), suggest the presence of mass transfer limitations. However, constant isomerization rates are still observed even at these higher isomerization rates, as long as the feed is deoxygenated and pretreated with alumina.

CONCLUSIONS

For 1-hexene isomerization on an industrial Pt/γ-Al$_2$O$_3$ catalyst, nearly constant catalyst activity has been demonstrated for 42 hours on stream with negligible coke laydown or loss in catalyst surface area. This activity maintenance is a result of the virtual elimination of feed peroxides and dissolved oxygen which catalyze the formation of oligomers in the fluid phase.

The invention has application also in processes including alkylation, disproportionation of aromatics and acylation reactions, as well as in nitration of aromatic compounds.

It will be appreciated by one skilled in the art that the invention may be practiced by pretreating hydrocarbon feed streams with any chemical agent that is operative to prevent peroxides (organic and inorganic) and any other impurities (including oxygen impurities) from participating in oligomer formation reactions. Such chemical agents would include, for example, molecular sieves such as zeolites.

It will also be appreciated by one skilled in the art that the invention may be employed to minimize catalyst deactivation rate and coke laydown in hydrocarbon processes in which the reaction conditions are not only supercritical and near-critical, but also sub-critical.

As used herein, the following terms have the indicated meanings:

1. The term oxygen impurities means impurities including dissolved oxygen.

2. The term "peroxides" means both organic and inorganic peroxides.

3. The term "hydrocarbon" means any compound containing hydrogen and carbon as a major species, especially olefins.

REFERENCES

Butt, J. B. and Petersen, E. E., 1988 *Activation, Deactivation and Poisoning of Catalysts*, Academic Press, San Diego, Calif. 64–119.

Dypvik, T., Holmen A., and Y. Ben Taarit, 1991, *Preprints-Division of Petroleum Chemistry, American Chemical Society*, 36, 4, 627–634.

Frank, J. P. and Martino, G. P., 1985, *Deactivation and Poisoning of Catalysts*, Oudar, J. and Wise, H., Eds.; Marcel Dekker Inc., New York and Basel, 20, 216–219

Gates, B. C., 1991, *Catalytic Chemistry*, John Wiley, New York

Ginosar, D. M. and Subramaniarn, B., 1995, *J. Catal.*, 152, 31–41.

Guisnet, M. and Magnoux, P., 1994, in *Catalyst Deactivation 1994*; Delmon, B. and G. F. Froment, Eds.; *Studies in Surface science and Catalysis*, 88 Elsevier, Amsterdam, 53–68.

Manos, G. and Hofmann, H., 1991, *Chem. Eng. Technol.*, 14, 73–78

Mushrush, G. W. and Speight, J. G., 1995, *Petroleum Products: Instability and incompatibility*, Taylor & Francis, U.S.

Niu, F. and Hofmann, H., 1995, *Applied Catalysis A: General*, 128, 107–118

Siam, S., and Subramaniam, B., 1991, *J. Catal.*, 131, 45

Subramaniam, B., and Jooma, A., 1995 *Innovations in Supercritical Fluids: Science and Technology*, Foster, N. R., and Hutchenson, K. W., Eds., ACS Symposium Series 608, Chapter 16, 246–256

The references appearing above and those appearing in the related application 08/424,872 are hereby incorporated herein by reference.

The theories expressed above are intended to assist with an understanding the invention and are subject to change or modification. Consequently, the theories expressed above are not intended to limit the scope of the invention as claimed below.

We claim:

1. In a method of carrying out a catalyzed reaction subject to catalyst deactivation by coke formation on the reaction catalyst including the steps of providing a feed stream including a reactant for the reaction and impurities comprising peroxide and oxygenate impurities, contacting said feed stream with a solid porous catalyst and causing the catalyzed reaction to occur and generate a reaction mixture, the improvement which comprises the steps of pretreating said feed stream to remove both oxygenate and peroxide impurities prior to said contacting step, and carrying out said contacting step at a catalyst temperature between 0.9–1.2 critical temperature of said reaction mixture.

2. The method of claim 1, said pretreating step comprising contacting said feed stream with a peroxide adsorption media.

3. The method of claim 2, said adsorption media comprising activated alumina.

4. The method of claim 1, said pretreating step comprising contacting said feed stream with helium to deoxygenate the feed stream.

5. The method of claim 1, the reaction conditions during said contacting step being subcritical.

6. The method of claim 1, said contacting step being supercritical.

7. The method of claim 1, said feed stream comprising hydrocarbon reactants.

8. The method of claim 1, including the step of carrying out said contacting step in a reactor having said catalyst therein, said reactor presenting passivated surfaces.

9. In a method of carrying out a catalyzed reaction subject to catalyst deactivation by coke formation on the reaction catalyst including the steps of providing a feed stream including a reactant for the reaction and containing inherent impurities comprising peroxide impurities, contacting said feed stream with a solid porous catalyst and causing the catalyzed reaction to occur and generate a reaction mixture, the improvement which comprises the steps of employing a deoxygenated feed stream having less than about 100 ppm of said inherent peroxide impurities therein, and carrying out said contacting step at a catalyst temperature between 0.9–1.2 critical temperature of said reaction mixture.

10. The method of claim 9, the reaction conditions during said contacting step being subcritical.

11. The method of claim 9, said contacting step being supercritical.

12. The method of claim 9, said feed stream comprising hydrocarbon reactants.

13. The method of claim 9, including the step of carrying out said contacting step in a reactor having said catalyst therein, said reactor presenting passivated surfaces.

* * * * *